(12) United States Patent
Shachan-Tov et al.

(10) Patent No.: US 11,339,164 B2
(45) Date of Patent: May 24, 2022

(54) CRYSTALLINE FORM E1 OF LAROTRECTINIB ETHANESULFONATE

(71) Applicant: ASSIA CHEMICAL INDUSTRIES LTD., Petach Tikva (IL)

(72) Inventors: Sharona Shachan-Tov, Kfar-Saba (IL); Doron Rudik, Modi'in (IL); Oshrat Frenkel, Modiin (IL); Rotem Sella-Erez, Tel-Aviv (IL); Maytal Piran, Rishon le Zion (IL); Ido Fuchs, Petach Tikva (IL)

(73) Assignee: ASSIA CHEMICAL INDUSTRIES LTD., Petach Tikva (IL)

( * ) Notice: Subject to any disclaimer, the term of this patent is extended or adjusted under 35 U.S.C. 154(b) by 92 days.

(21) Appl. No.: 16/754,845

(22) PCT Filed: Oct. 31, 2018

(86) PCT No.: PCT/US2018/058316
§ 371 (c)(1),
(2) Date: Apr. 9, 2020

(87) PCT Pub. No.: WO2019/089668
PCT Pub. Date: May 9, 2019

(65) Prior Publication Data
US 2020/0255435 A1    Aug. 13, 2020

Related U.S. Application Data

(60) Provisional application No. 62/579,457, filed on Oct. 31, 2017, provisional application No. 62/589,736, filed on Nov. 22, 2017, provisional application No. 62/595,682, filed on Dec. 7, 2017.

(51) Int. Cl.
*A61K 31/519* (2006.01)
*C07D 487/04* (2006.01)

(52) U.S. Cl.
CPC ........ *C07D 487/04* (2013.01); *C07B 2200/13* (2013.01)

(58) Field of Classification Search
CPC ........................... A61K 31/519; C07D 487/04
USPC ...................................... 514/259.3; 544/281
See application file for complete search history.

(56) References Cited

U.S. PATENT DOCUMENTS 8,513,263 B2    8/2013    Haas et al.
9,127,013 B2    9/2015    Haas et al.

FOREIGN PATENT DOCUMENTS

WO    2016077841 A1    5/2016

OTHER PUBLICATIONS

International Search Report and Written Opinion of the International Searching Authority issued in corresponding Appl. No. PCT/US2018/058316 dated Jan. 15, 2019 (12 pages).

*Primary Examiner* — Douglas M Willis
(74) *Attorney, Agent, or Firm* — Carter, DeLuca & Farrell LLP (57) ABSTRACT

Salts and solid state forms of Larotrectinib, processes for preparation thereof, pharmaceutical compositions thereof, and uses thereof are disclosed.

7 Claims, 5 Drawing Sheets

Figure 1: An XRPD pattern of Form E1 of Larotrectinib ethansulfonate.

Figure 2: An XRPD pattern of Form M1 of Larotrectinib methansulfonate.

Figure 3: An XRPD pattern of Form L1 of Larotrectinib hydrogen sulfate.

Figure 4: An XRPD pattern of Form L2 of Larotrectinib hydrogen sulfate.

Figure 5: Figure 5 shows SEM images of Form E1 of Larotrectinib ethanesulfonate, magnification 500X

CRYSTALLINE FORM E1 OF LAROTRECTINIB ETHANESULFONATE

CROSS REFERENCE TO RELATED APPLICATIONS

This application is a National Stage Application of, and claims priority to and the benefit of, International Patent Application No. PCT/US2018/058316 filed on Oct. 31, 2018, which, in turn, claims the benefit of, and priority to, U.S. Provisional Application No. 62/579,457 filed Oct. 31, 2017, U.S. Provisional Application No. 62/589,736 filed Nov. 22, 2017, and U.S. Provisional Application No. 62/595,682 filed Dec. 7, 2017, the entire disclosures of each of which are incorporated by reference herein.

TECHNICAL FIELD

The present disclosure relates to new salts of Larotrectinib and solid state forms thereof, processes for the preparation thereof, pharmaceutical formulations/compositions thereof, and methods of use thereof.

BACKGROUND

Larotrectinib, (S)—N-(5-((R)-2-(2,5-difluorophenyl)pyrrolidin-1-yl)pyrazolo[1,5-a]pyrimidin-3-yl)-3-hydroxypyrrolidine-1-carboxamide, having the following formula:

is an ATP-competitive inhibitor of tropomyosin-related kinase (TRK) family of receptor kinases, which is being developed by Array BioPharma Inc. for the treatment of cancer.

Larotrectinib was described in U.S. Pat. No. 8,513,263. The hydrogen sulfate salt of Larotrectinib is described in U.S. Pat. No. 9,127,013. A crystalline form HS-1 of the Hydrogen Sulfate is described in International Application No. WO2016077841.

Polymorphism, the occurrence of different crystal forms, is a property of some molecules and molecular complexes. A single compound, like Larotrectinib, may give rise to a variety of polymorphs having distinct crystal structures and physical properties like melting point, thermal behaviors (e.g. measured by thermogravimetric analysis—"TGA", or differential scanning calorimetry—"DSC"), X-ray powder diffraction (XRPD) pattern, infrared absorption fingerprint, Raman absorption fingerprint, and solid state ($^{13}$C—) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, improving the dissolution profile, or improving stability (polymorphic as well as chemical stability) and shelf-life. These variations in the properties of different salts and solid state forms may also provide improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to use variations in the properties and characteristics of a solid active pharmaceutical ingredient for providing an improved product.

Discovering new salts and solid state forms and solvates of a pharmaceutical product can provide materials having desirable processing properties, such as ease of handling, ease of processing, storage stability, and ease of purification or as desirable intermediate crystal forms that facilitate conversion to other salts or polymorphic forms. New salts, polymorphic forms and solvates of a pharmaceutically useful compound can also provide an opportunity to improve the performance characteristics of a pharmaceutical product (dissolution profile, bioavailability, etc.). It enlarges the repertoire of materials that a formulation scientist has available for formulation optimization, for example by providing a product with different properties, e.g., a different crystal habit, higher crystallinity or polymorphic stability which may offer better processing or handling characteristics, improved dissolution profile, or improved shelf-life. For at least these reasons, there is a need for additional salts and solid state forms (including solvated forms) of Larotrectinib.

SUMMARY

The present disclosure relates to Larotrectinib salts, in particular to ethanesulfonate, methanesulfonate and hydrogen sulfate salts, and solid state forms thereof, The present disclosure also relates to the uses of Larotrectinib salts and solid state forms thereof of the present disclosure, for preparing Larotrectinib or other salts of Larotrectinib, and solid state forms thereof.

The present disclosure also encompasses the uses of the above described Larotrectinib salts and solid state forms thereof for the preparation of pharmaceutical compositions and/or formulations.

In another embodiment, the present disclosure encompasses pharmaceutical compositions comprising the above described Larotrectinib salts and solid state forms thereof.

In yet another embodiment, the present disclosure encompasses pharmaceutical formulations comprising the above described Larotrectinib salts and solid state forms thereof, and at least one pharmaceutically acceptable excipient.

The present disclosure further encompasses processes to prepare said pharmaceutical formulations of Larotrectinib salts including combining the crystalline form of any one of the Larotrectinib salt of the present disclosure, or pharmaceutical compositions including it, and at least one pharmaceutically acceptable excipient.

Larotrectinib salts and solid state forms thereof defined herein as well as the pharmaceutical compositions and formulations of Larotrectinib salts and solid state forms thereof can be used as medicaments, particularly for the treatment of Cancer, including administering a therapeutically effective amount of Larotrectinib salts and solid state forms thereof of the present disclosure, or at least one of the above pharmaceutical compositions or formulations, to a subject suffering from Cancer, or otherwise in need of the treatment.

The present disclosure also provides the uses of Larotrectinib salts and the solid state forms thereof of the present disclosure, or at least one of the above pharmaceutical compositions or formulations, for the manufacture of medicaments for treating Cancer.

In another aspect, the present disclosure encompasses the above Larotrectinib salts and solid state forms thereof for use in medicine, preferably for the treatment of Cancer.

DETAILED DESCRIPTION OF ILLUSTRATIVE EMBODIMENTS

The present disclosure relates to salts of Larotrectinib, in particular to ethanesulfonate, methanesufonate and hydrogen sulfate salt and solid state forms thereof, to processes for preparation thereof and to pharmaceutical compositions and formulations including them. The disclosure also relates to the conversion of Larotrectinib salts and solid state forms thereof of the present disclosure to Larotrectinib or other salts and/or solid state form of Larotrectinib, such as Larotrectinib hydrogen sulfate.

Larotrectinib salts and the solid state form thereof according to the present disclosure may have advantageous properties selected from at least one of: chemical or polymorphic purity, flowability, solubility, dissolution rate, bioavailability, morphology or crystal habit, stability—such as chemical stability as well as thermal and mechanical stability with respect to polymorphic conversion, stability towards dehydration and/or storage stability, a lower degree of hygroscopicity, low content of residual solvents, adhesive tendencies and advantageous processing and handling characteristics such as compressibility, and bulk density.

A crystal form may be referred to herein as being characterized by graphical data "as depicted in" a Figure. Such data include, for example, powder X-ray diffractograms and solid state NMR spectra. As is well-known in the art, the graphical data potentially provides additional technical information to further define the respective solid state form (a so-called "fingerprint") which can not necessarily be described by reference to numerical values or peak positions alone. In any event, the skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms.

Larotrectinib salts or solid state form thereof referred to herein as being characterized by graphical data "as depicted in" a Figure will thus be understood to include any Larotrectinib salt, characterized with the graphical data having such small variations, as are well known to the skilled person, in comparison with the Figure.

A solid state form (or polymorph) may be referred to herein as polymorphically pure or as substantially free of any other solid state (or polymorphic) forms. As used herein in this context, the expression "substantially free of any other forms" will be understood to mean that the solid state form contains about 20% (w/w) or less, about 10% (w/w) or less, about 5% (w/w) or less, about 2% (w/w) or less, about 1% (w/w) or less, or about 0% of any other forms of the subject compound as measured, for example, by XRPD. Thus, solid states of Larotrectinib salts described herein as substantially free of any other solid state forms would be understood to contain greater than about 80% (w/w), greater than about 90% (w/w), greater than about 95% (w/w), greater than about 98% (w/w), greater than about 99% (w/w), or about 100% of the subject solid state form of Larotrectinib salts. In some embodiments of the disclosure, the described solid state forms of Larotrectinib salts may contain from about 1% to about 20% (w/w), from about 5% to about 20% (w/w), or from about 5% to about 10% (w/w) of one or more solid state forms of Larotrectinib salts of the present disclosure or other salts of Larotrectinib.

As used herein, unless stated otherwise, XRPD peaks reported herein are measured using CuKα radiation, λ=1.5418 Å, in some cases, XRPD peaks reported herein are measured using CuK α radiation, λ=1.5418 Å, at a temperature of 25±3° C.

As used herein, the term "isolated" in reference to solid state forms of Larotrectinib salts of the present disclosure corresponds to solid state form of Larotrectinib salts that is physically separated from the reaction mixture in which it is formed.

A thing, e.g., a reaction mixture, may be characterized herein as being at, or allowed to come to "room temperature", often abbreviated "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

A process or step may be referred to herein as being carried out "overnight." This refers to a time interval, e.g., for the process or step, that spans the time during the night, when that process or step may not be actively observed. This time interval is from about 8 to about 20 hours, or about 10 to about 18 hours, typically about 16 hours.

As used herein, the expression "wet crystalline form" refers to a polymorph that was not dried using any conventional techniques to remove residual solvent. Examples for such conventional techniques can be, but not limited to, evaporation, vacuum drying, oven drying, drying under nitrogen flow, and the like.

As used herein, the expression "dry crystalline form" refers to a polymorph that was dried using any conventional techniques to remove residual solvent. Examples of such conventional techniques can be, but are not limited to, evaporation, vacuum drying, oven drying, drying under nitrogen flow, and the like.

As used herein, and unless stated otherwise, the term "anhydrous" in relation to a Larotrectinib salts or a crystalline Larotrectinib salts relates to a Larotrectinib salts or crystalline Larotrectinib salts which does not include any crystalline water (or other solvents) in a defined, stoichiometric amount within the crystal. Moreover, an "anhydrous" form does not contain more than about 1% (w/w) of either water or organic solvents as measured for example by TGA.

The term "solvate", as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

The amount of solvent employed in a chemical process, e.g., a reaction or a crystallization may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding (methyl tert-butyl ether) MTBE (1.5 v/v) to a 100 ml reaction mixture would indicate that 150 mL of MTBE was added.

As used herein the term non-hygroscopic in relation to Larotrectinib salts or crystalline forms thereof, refers to less than about 1.0% (w/w) absorption of water at about 25° C. and about 80% relative humidity (RH), by the Larotrectinib salts or crystalline forms thereof as determined for example by TGA. Water can be for example atmospheric water.

As used herein, the term "reduced pressure" refers to a pressure of about 10 mbar to about 500 mbar.

As used herein, and unless indicated otherwise, the term "thermo-dynamical stability" in relation to salts and solid state forms of Larotrectinib salts refers to resistance of the solid state form to polymorphic conversion under certain conditions, for example, heating, melting or dissolving. In some embodiments, the term refers to less than about 20% (w/w), about 10% (w/w), about 5% (w/w), about 1% (w/w), about 0.5% (w/w), or about 0% (w/w) conversion of the crystalline Larotrectinib salts to any other solid state form of Larotrectinib salts of the present disclosure or other salt thereof as measured by XRPD. In some embodiments, the conversion is about 1% (w/w) to about 20% (w/w), about 1% (w/w) to about 10% (w/w) or about 1% (w/w) to about 5% (w/w).

The present disclosure includes Larotrectinib ethanesulfonate, methanesulfonate and hydrogen sulfate as well as solid state forms thereof.

Figure 1:
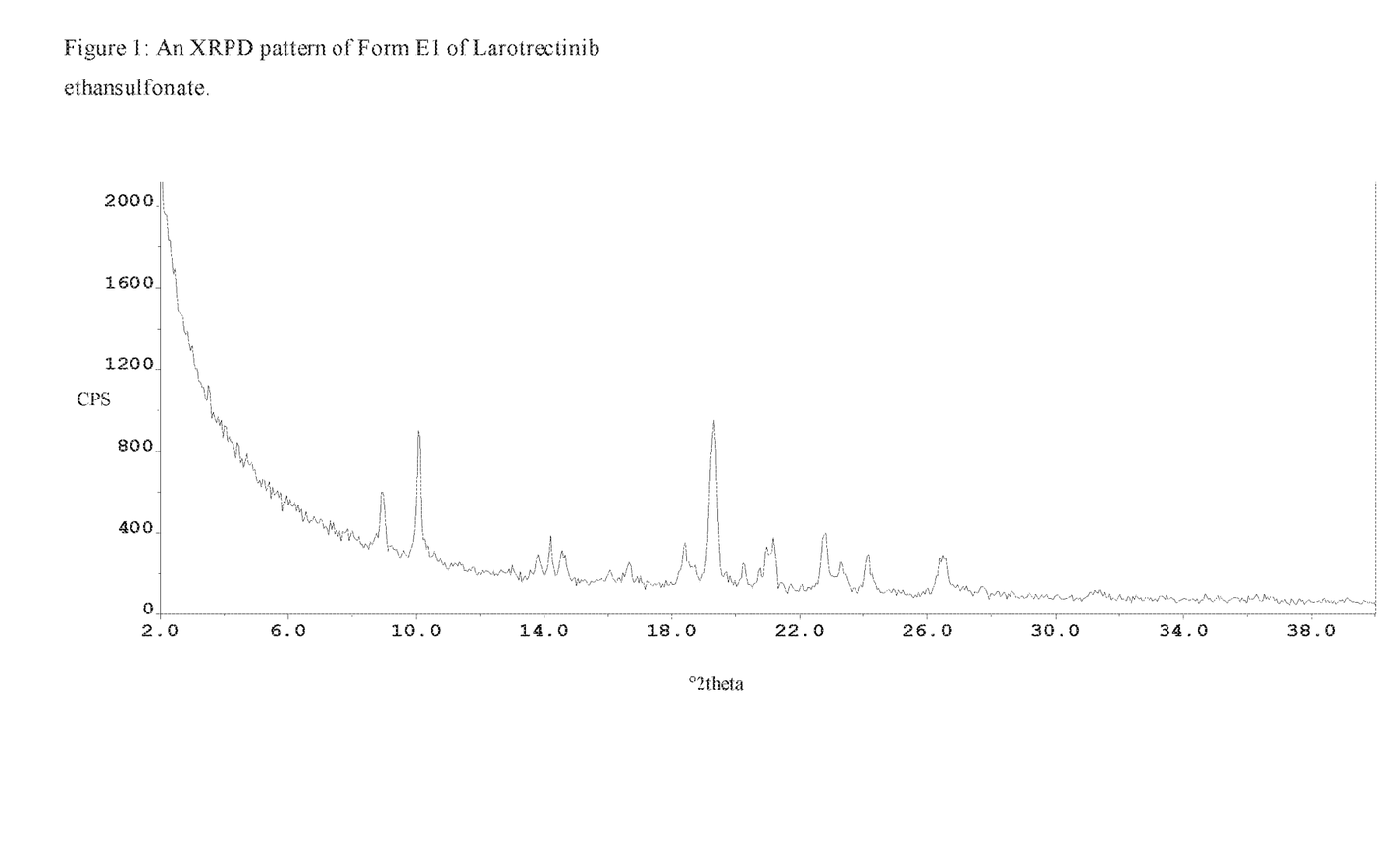
FIG. 1 shows an X-ray powder diffraction (XRPD) pattern of Form E1 of Larotrectinib ethanesulfonate.

The present disclosure includes a crystalline form of Larotrectinib ethanesulfonate designated as Form E1. The crystalline Form E1 of Larotrectinib ethanesulfonate can be characterized by data selected from one or more of the following: an XRPD pattern having peaks at 8.9, 10.0, 13.8, 14.2 and 14.6 degrees 2-theta±0.2 degrees 2-theta; an XRPD pattern substantially as depicted in FIG. 1; or combinations of these data.

Crystalline Form E1 of Larotrectinib ethanesulfonate may be further characterized by data selected from one or more of the following: an XRPD pattern having peaks at 8.9, 10.0, 13.8, 14.2 and 14.6 degrees two theta±0.2 degrees two theta; and also having one, two, three, four or five additional peaks selected from 18.4, 19.3, 22.8, 24.1 and 26.5 degrees two theta±0.2 degrees two theta; or combinations of these data.

In some embodiments the crystalline Form E1 of Larotrectinib ethanesulfonate may be anhydrous.

Figure 5:
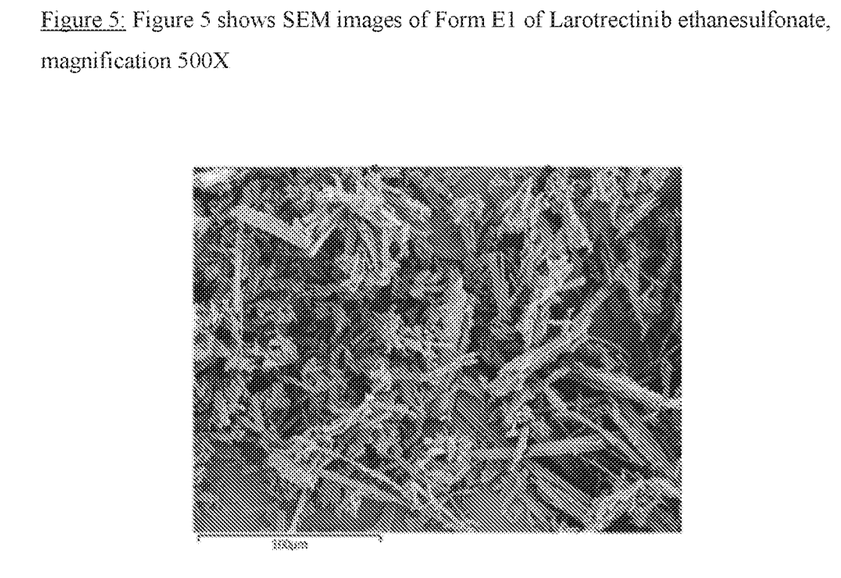
FIG. 5 shows SEM images of Form E1 of Larotrectinib ethanesulfonate, magnification 500×.

In some embodiments, the crystalline Form E1 as defined according to any aspect or embodiment described herein, may be provided in a particular morphology. In particular, Form E1 exhibits rod like morphology (FIG. 5) having better compressibility properties; leading to a compacted and formed tablet.

Figure 2:
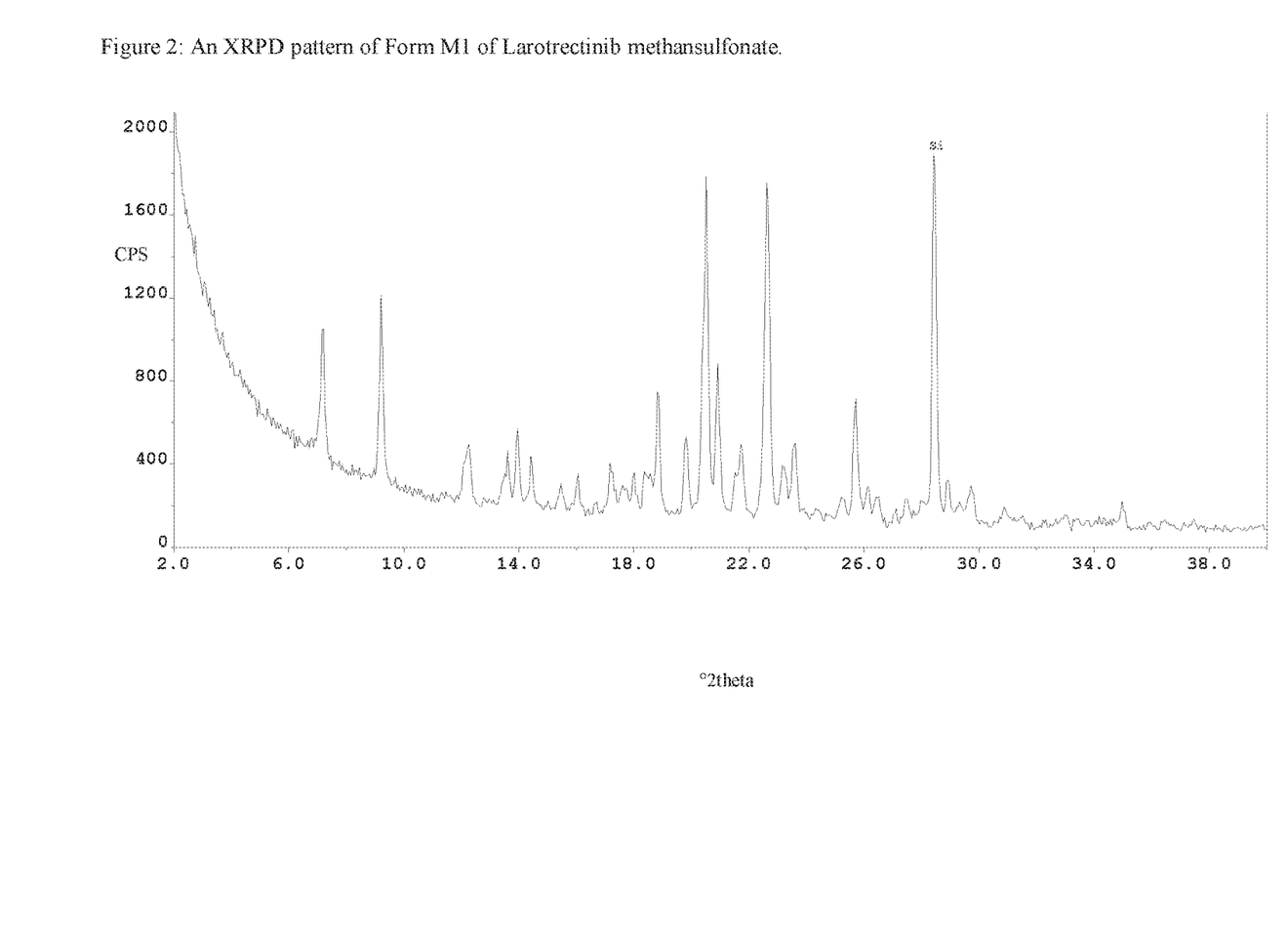
FIG. 2 shows an XRPD pattern of Form M1 of Larotrectinib methanesulfonate.

The present disclosure further includes a crystalline form of Larotrectinib methanesulfonate designated as Form M1. The crystalline Form M1 of Larotrectinib methanesulfonate can be characterized by data selected from one or more of the following: an XRPD pattern having peaks at 7.2, 9.3, 17.2, 18.9 and 22.7 degrees 2-theta±0.2 degrees 2-theta; an XRPD pattern substantially as depicted in FIG. 2; or combinations of these data.

Crystalline Form M1 of Larotrectinib methanesulfonate may be further characterized by data selected from one or more of the following: an XRPD pattern having peaks at 7.2, 9.3, 17.2, 18.9 and 22.7 degrees 2-theta±0.2 degrees 2-theta; and also having one, two, three, four or five additional peaks selected from 14.0, 15.5, 19.8, 20.5 and 23.6 degrees 2-theta±0.2 degrees 2-theta; or combinations of these data.

Figure 3:
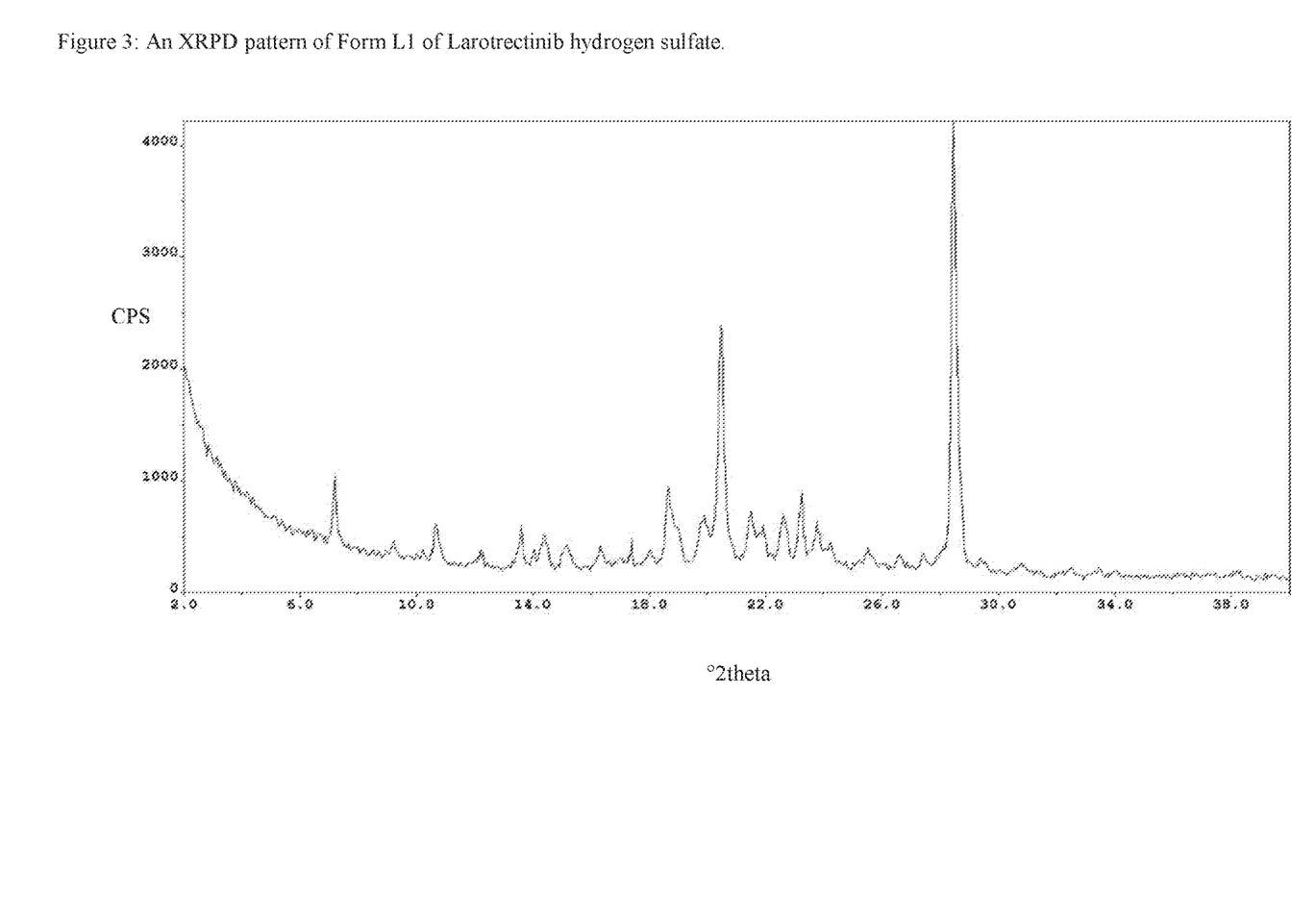
FIG. 3 shows an XRPD pattern of Form L1 of Larotrectinib hydrogen sulfate.

The present disclosure includes a crystalline form of Larotrectinib hydrogen sulfate designated as Form L1. The crystalline Form L1 of Larotrectinib hydrogen sulfate can be characterized by data selected from one or more of the following: an XRPD pattern having peaks at 7.2, 9.2, 12.3, 20.4 and 22.6 degrees 2-theta±0.2 degrees 2-theta; an XRPD pattern substantially as depicted in FIG. 3; or combinations of these data.

Crystalline Form L1 of Larotrectinib hydrogen sulfate may be further characterized by data selected from one or more of the following: an XRPD pattern having peaks at 7.2, 9.2, 12.3, 20.4 and 22.6 degrees 2-theta±0.2 degrees 2-theta; and also having one, two, three, four or five additional peaks selected from 13.6, 14.1, 14.4, 17.4 and 18.0 degrees 2-theta±0.2 degrees 2-theta; or combinations of these data.

Figure 4:
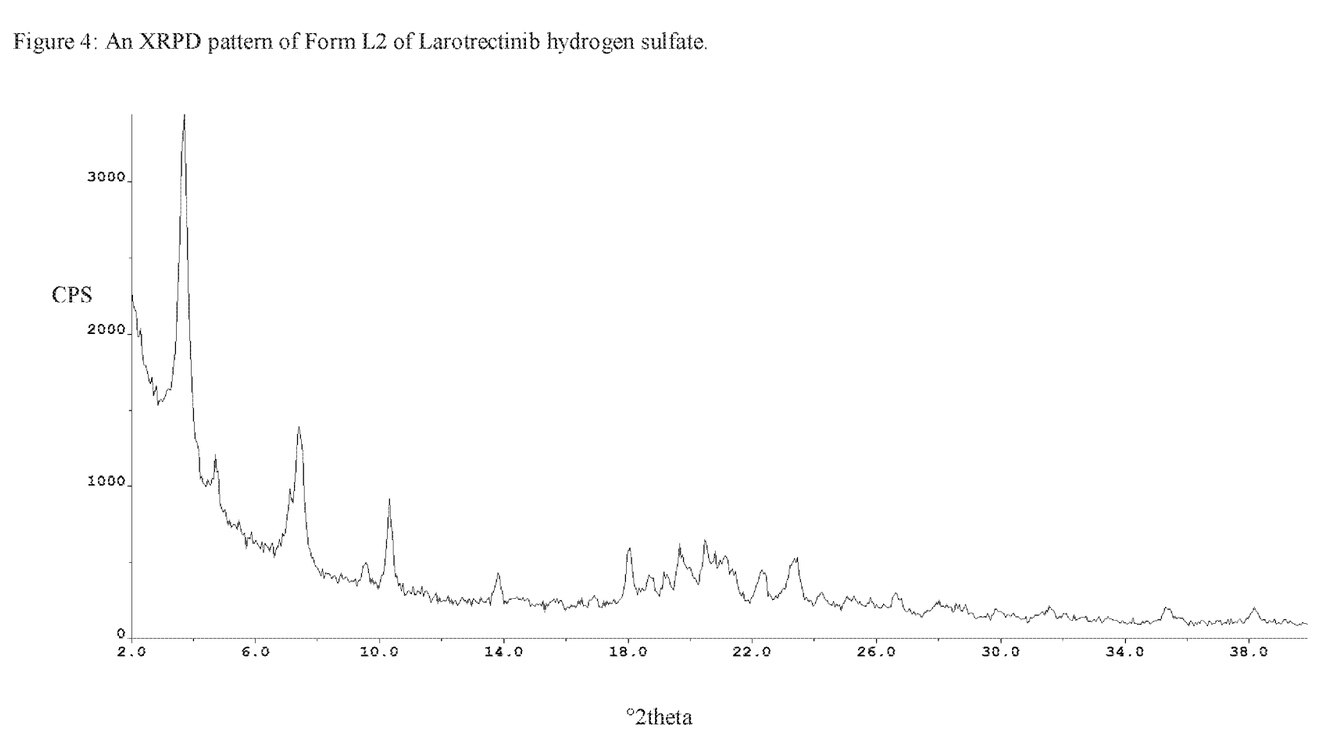
FIG. 4 shows an XRPD pattern of Form L2 of Larotrectinib hydrogen sulfate.

The present disclosure further includes a crystalline form of Larotrectinib hydrogen sulfate designated as Form L2. The crystalline Form L2 of Larotrectinib hydrogen sulfate can be characterized by data selected from one or more of the following: an XRPD pattern having peaks at 3.7, 7.4, 9.5, 18.0 and 20.5 degrees 2-theta±0.2 degrees 2-theta; an XRPD pattern substantially as depicted in FIG. 4; or combinations of these data.

Crystalline Form L2 of Larotrectinib hydrogen sulfate may be further characterized by data selected from one or more of the following: an XRPD pattern having peaks at 3.7, 7.4, 9.5, 18.0 and 20.5 degrees 2-theta±0.2 degrees 2-theta; and also having one, two, three, four or five additional peaks selected from 4.8, 10.3, 13.9, 19.7 and 23.4 degrees 2-theta±0.2 degrees 2-theta; or combinations of these data.

The present disclosure also provides the use of Larotrectinib salts and solid state forms thereof of the present disclosure for preparing other solid state forms of Larotrectinib ethanesulfonate, Larotrectinib methanesulfonate or Larotrectinib hydrogen sulfate, respectively, solid state forms of Larotrectinib and/or solid state forms of other Larotrectinib salts.

Another embodiment the present disclosure encompasses the use of the above described solid state forms of Larotrectinib ethanesulfonate, methanesulfonate or hydrogen sulfate salts, for the preparation of pharmaceutical compositions and/or formulations.

The present disclosure further provides pharmaceutical compositions including the solid state form of Larotrectinib salts described above.

In yet another embodiment, the present disclosure encompasses pharmaceutical formulations including the above described solid state forms of Larotrectinib ethanesulfonate, Larotrectinib methanesulfonate or Larotrectinib hydrogen sulfate, and at least one pharmaceutically acceptable excipient.

The present disclosure moreover encompasses processes to prepare said formulations of Larotrectinib salts and solid state forms thereof including combining Larotrectinib ethanesulfonate, Larotrectinib methanesulfonate, Larotrectinib hydrogen sulfate, or solid state forms thereof, and at least one pharmaceutically acceptable excipient.

In another embodiment, the present disclosure encompasses the above described Larotrectinib salts and solid state forms thereof, for use in medicine, in embodiments for the treatment Cancer.

The present disclosure also provides methods of treating Cancer, including administering a therapeutically effective amount of the Larotrectinib salts and solid state forms thereof of the present disclosure, or at least one of the above pharmaceutical compositions or formulations, to a subject suffering from Cancer, or otherwise in need of the treatment.

The present disclosure also provides the use of Larotrectinib salts or solid state forms thereof of the present disclosure, or at least one of the above pharmaceutical compositions or formulations, for the manufacture of a medicament for treating Cancer.

The present disclosure further provides the Larotrectinib salts and solid state forms thereof of the present disclosure, or the above pharmaceutical compositions or formulations for use in medicine, especially for treating Cancer.

Having described the disclosure with reference to certain preferred embodiments, other embodiments will become apparent to one skilled in the art from consideration of the specification. The disclosure is further illustrated by reference to the following examples describing in detail the preparation of the composition and methods of use of the disclosure. It will be apparent to those skilled in the art that many modifications, both to materials and methods, may be practiced without departing from the scope of the disclosure.

Analytical Methods

X-ray Powder diffraction pattern ("XRPD") method:

Powder X-ray Diffraction was performed on ARL (SCINTAG) powder X-Ray diffractometer model X'TRA equipped with a solid state detector. Copper radiation of 1.5418 Å was used. Scanning parameters: range: 2-40 degrees two-theta; scan mode: continuous scan; step size: 0.05°, and a rate of 3 deg/min. The peak at about 28.5° is attributed to silicon powder added as an internal standard.

Larotrectinib base, which is used as the starting material, may be prepared for example according to the processes described in U.S. Pat. No. 8,513,263.

Amorphous form of Larotrectinib hydrogen sulfate, which is used as the starting material, can be prepared for example according to the process described in Example 3 of U.S. Patent Application Publication No. 2016/0137654.

EXAMPLES

Example 1: Preparation of form E1 of Larotrectinib Ethanesulfonate

To a stirred solution of Larotrectinib free base (30 mg, 1 eq) in methanol (0.5 mL) a solution of ethansulfonic acid (6.0 µL, 1.07 eq) in methanol (0.6 mL) was added. The obtained clear solution was stirred at RT for 0.5 hour and then concentrated by vacuum oven at 40° C. overnight to produce oil. The residue was slurried with ethyl acetate (0.3 mL) at 50° C. for 17 hours and then cooled to RT and stirred for 1 hour. The solid was filtered and characterized by X-ray powder diffraction to give Larotrectinib ethanesulfonate salt form E1 as depicted in FIG. 1.

Example 2: Preparation of form E1 of Larotrectinib Ethanesulfonate

To a stirred solution of Larotrectinib free base (300 mg, 1 eq) in methanol (0.6 mL) ethansulfonic acid (61 µL, 1.07 eq) was added. The obtained clear solution was stirred for 5 minutes and then evaporated to produce oil. The oily residue was mixed with ethyl acetate (3 mL) and then evaporated to give oil. The oily residue was mixed again with ethyl acetate (3 mL) and stirred at 78° C. for 3 hours to obtain a slurry mixture. The solid was filtered and to give Larotrectinib ethanesulfonate salt form E1, as was confirmed by XRPD.

Example 3: Preparation of form M1 of Larotrectinib Methanesulfonate

A vial with magnetic stirrer was charged with Larotrectinib free base (200 mg, 1 eq) and ethyl acetate (2 mL) and heated to 50° C. until clear solution was obtained. Then methanesulfonic acid (30.6 µL, 1.07 eq) was added dropwise to the stirred solution to give an oily precipitant. The mixture was further stirred for 2 days at RT to obtain a solid which was filtered and characterized by X-ray powder diffractogram to give Larotrectinib methanesulfonate form M1 as depicted in FIG. 2.

Example 4: Preparation of form L1 of Larotrectinib Hydrogen Sulfate

Amorphous Larotrectinib hydrogen sulfate (50 mg) was loaded in a vial and n-butanol (10 vol) was added to obtain a slurry mixture. The slurry mixture was cooled to −10° C. and stirred for 72 hours. The solid was then filtered and characterized by X-Ray powder diffraction to give Larotrectinib hydrogen sulfate form L1, as was confirmed by XRPD.

Example 5: Preparation of Form L1 of Larotrectinib Hydrogen Sulfate

Amorphous Larotrectinib hydrogen sulfate (50 mg) was loaded in a vial and isobutanol (10 vol) was added to obtain a slurry mixture. The slurry mixture was cooled to −10° C. and stirred for 72 hours. The solid was then filtered and characterized by X-Ray powder diffraction to give Larotrectinib hydrogen sulfate form L1, as was confirmed by XRPD.

Example 6: Preparation of Form L1 of Larotrectinib Hydrogen Sulfate

Amorphous Larotrectinib hydrogen sulfate (50 mg) was loaded in a vial and 1,2-dichloroethane (10 vol) was added to obtain a slurry mixture. The mixture was cooled to −10° C. and stirred for 48 hours to produce a gel like material. The mixture was heated to RT and stirred for 30 minutes to obtain solid powdered slurry. The solid was then filtered and characterized by X-Ray powder diffraction to give Larotrectinib hydrogen sulfate form L1, as was confirmed by XRPD.

Example 7: Preparation of Form L1 of Larotrectinib Hydrogen Sulfate

Amorphous Larotrectinib hydrogen sulfate (114 mg) was loaded in a vial and methanol was added at RT (1 vol) to get clear solution. Then MTBE (300 µL) was added to the solution and after several seconds of stirring at RT a gel like material was observed. The mixture was stirred at RT for 1 hour to obtain a solid material which was then filtered and characterized by X-Ray powder diffraction to give Larotrectinib hydrogen sulfate form L1, as was confirmed by XRPD.

Example 8: Preparation of Form L1 of Larotrectinib Hydrogen Sulfate

Amorphous Larotrectinib hydrogen sulfate (880 mg) was mixed with propanol (10 vol) at RT to obtain clear solution. 670 µL of the clear solution was set in a small open vial within a larger vial containing 2.5 mL of heptane. The larger vial was purged by nitrogen atmosphere and then sealed and kept for 6 days at RT to obtain a solid material in the small vial. The solid was then separated from the solution by decantation and kept under vacuum overnight. The solid obtained was characterized by X-Ray powder diffraction to give Larotrectinib hydrogen sulfate form L1, as was confirmed by XRPD.

Example 9: Preparation of Form L1 of Larotrectinib Hydrogen Sulfate

Amorphous Larotrectinib hydrogen sulfate (880 mg) was mixed with propanol (10 vol) at RT to obtain clear solution. 670 µL of the clear solution was set in a small open vial within a larger vial containing 2.5 mL of hexane. The larger vial was purged by nitrogen atmosphere and then sealed and kept for 6 days at RT to obtain a solid material in the small vial. The solid was then separated from the solution by decantation and kept under vacuum overnight. The solid obtained was characterized by X-Ray powder diffraction to give Larotrectinib hydrogen sulfate form L1, as depicted in FIG. 3.

Example 10: Preparation of Form L1 of Larotrectinib Hydrogen Sulfate

Amorphous Larotrectinib hydrogen sulfate (880 mg) was mixed with propanol (10 vol) at RT to obtain clear solution. 670 µL of the clear solution was set in a small open vial within a larger vial containing 2.5 mL of pentane. The larger vial was purged by nitrogen atmosphere and then sealed and kept for 6 days at RT to obtain a solid material in the small vial. The solid was then separated from the solution by decantation and kept under vacuum overnight. The solid obtained was characterized by X-Ray powder diffraction to give Larotrectinib hydrogen sulfate form L1, as was confirmed by XRPD.

Example 11: Preparation of Form L1 of Larotrectinib Hydrogen Sulfate

Amorphous Larotrectinib hydrogen sulfate (1.2 g) was mixed with methanol (2 vol) at RT to obtain a clear solution. 200 µL of the clear solution was set in a small open vial within a larger vial containing 2.5 mL of Cyclopentylmethyl ether (CPME). The larger vial was purged by nitrogen atmosphere and then sealed and kept for 6 days at RT to obtain a solid material in the small vial. The solid was then separated from the solution by decantation and kept under vacuum overnight. The solid obtained was characterized by X-Ray powder diffraction to give Larotrectinib hydrogen sulfate form L1, as was confirmed by XRPD.

Example 12: Preparation of Form L2 of Larotrectinib Hydrogen Sulfate

Amorphous Larotrectinib hydrogen sulfate (50 mg) was loaded in a glass vial equipped with magnetic stirrer. t-Butanol (10 vol) and 10% v/v of water were then added to obtain clear solution. The solution was then stirred for 24 hours at 4° C. and additional 24 hours at −10° C. t-Butanol (5 vol) was added then to the clear solution and the solution was stirred at 4° C. for 16 hours to obtain a solid. The solid was then filtered and characterized by X-Ray powder diffraction to give Larotrectinib hydrogen sulfate form L2, as depicted in FIG. 4.

Example 13: Preparation of Form L2 of Larotrectinib Hydrogen Sulfate

Amorphous Larotrectinib hydrogen sulfate (305 mg) was loaded in a glass vial equipped with magnetic stirrer. t-Butanol (15 vol) and water (1 vol) were then added and the mixture was stirred until clear solution was obtained. The solution was then cooled to 0° C. and stirred for 16 hours, resulting in a gel-like solid, which was washed with small amount of t-butanol. The solid obtained was then filtered and characterized by X-Ray powder diffraction to give Larotrectinib hydrogen sulfate form L2, as was confirmed by XRPD.

Example 14: Preparation of Form E1 of Larotrectinib Ethanesulfonate

To a stirred solution of Larotrectinib free base (1.0 g, 1 eq) in methanol (2.0 mL) ethansulfonic acid, 90% (232.7 µL, 1.1 eq) was added. The obtained clear solution was stirred for 5 minutes and then evaporated to produce oil. The oily residue was mixed with ethyl acetate (11 mL) and stirred at 78° C. for 2 hours to obtain a suspension. The suspension was cooled down to room temperature. The obtained solid was filtered, washed with 2 mL of ethyl acetate and dried in vacuum oven at 40° C. for 5 hours. The solid was characterized by X-ray powder diffraction to give Larotrectinib ethanesulfonate salt form E1.

The invention claimed is:

1. Crystalline Form E1 of Larotrectinib ethanesulfonate of the formula:

wherein the crystalline Form E1 is characterized by a powder X-ray diffraction pattern comprising characteristic peaks (°2θ) at 8.9°±0.2 °2θ, 10.0°±0.2 °2θ, 13.8°±0.2 °2θ, 14.2°±0.2 °2θ, and 14.6°±0.2 °2θ.

2. The crystalline Form E1 of Larotrectinib ethanesulfonate according to claim 1, wherein the crystalline Form E1 is further characterized by a powder X-ray diffraction pattern comprising one, two, three, four, or five additional characteristic peaks (°2θ) selected from the group consisting of 18.4°±0.2 °2θ, 19.3°±0.2 °2θ, 22.8°±0.2 °2θ, 24.1°±0.2 °2θ, and 26.5°±0.2 °2θ.

3. The crystalline Form E1 of Larotrectinib ethanesulfonate according to claim 1, wherein the crystalline Form E1 is further characterized by a powder X-ray diffraction pattern as depicted in FIG. 1.

4. A medicament comprising the crystalline Form E1 of Larotrectinib ethanesulfonate according to claim 1.

5. A pharmaceutical composition comprising at least one pharmaceutically acceptable excipient and the crystalline Form E1 of Larotrectinib ethanesulfonate according to claim 1.

6. A method for treating cancer in a subject suffering from cancer, wherein the method comprises administering to the subject in need of such treatment a therapeutically effective amount of the crystalline Form E1 of Larotrectinib ethanesulfonate according to claim 1.

7. A process for preparing the medicament according to claim 4, wherein the process comprises combining at least one pharmaceutically acceptable excipient with the crystalline Form E1 of Larotrectinib ethanesulfonate according to claim 1.

\* \* \* \* \*